Figure 1:
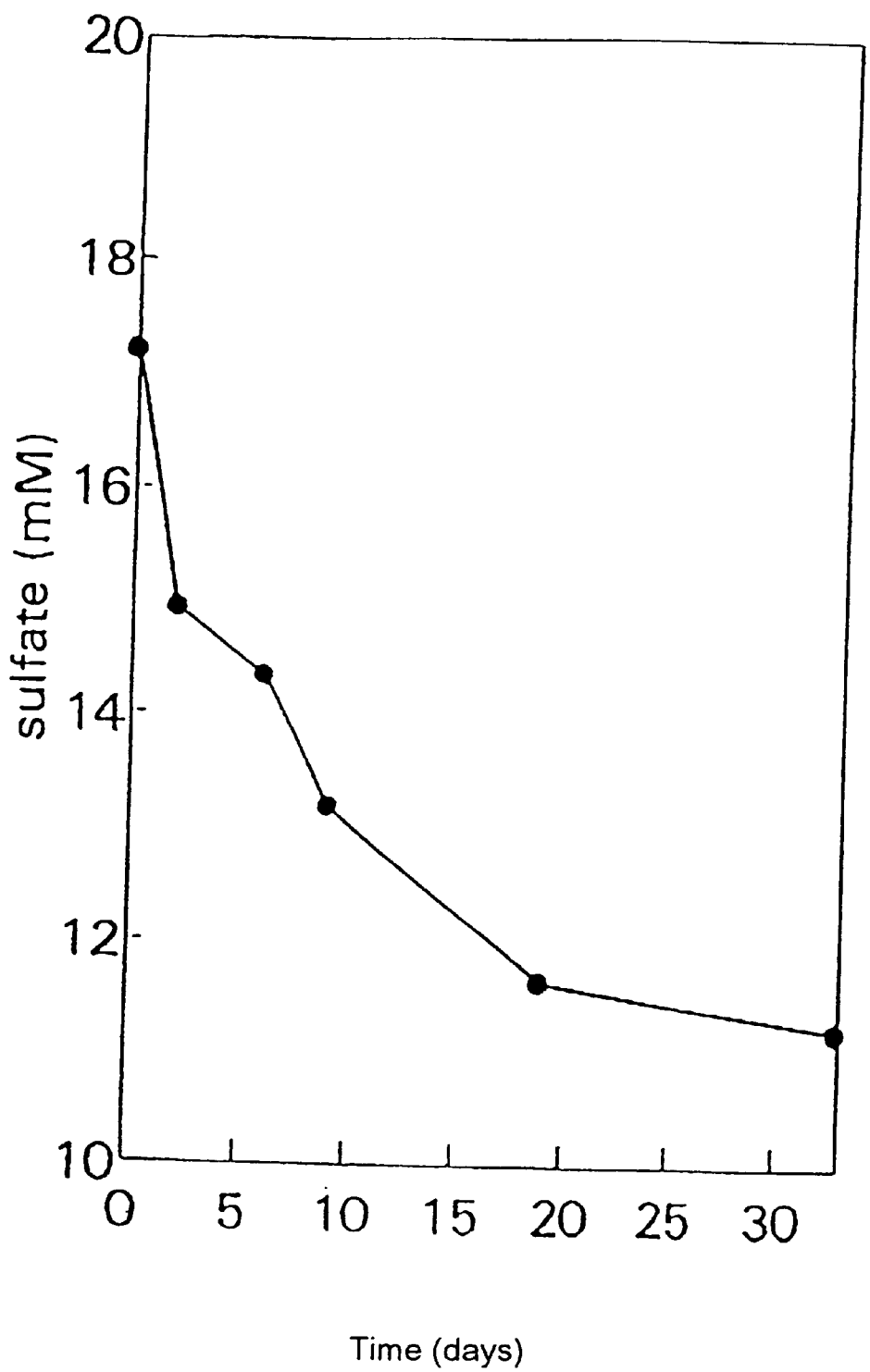

United States Patent [19]
Hard et al.

[11] Patent Number: 6,080,572
[45] Date of Patent: Jun. 27, 2000

[54] SULPHATE-REDUCING BACTERIAL STRAINS AND THEIR USE IN THE DECONTAMINATION OF WATER CONTAMINATED WITH SULPHURIC ACID, METALS AND RADIOACTIVE SUBSTANCES

[75] Inventors: Barbara Hard; Wolfgang Babel; Silke Friedrich, all of Leipzig, Germany

[73] Assignee: UFZ-Umweltforschungszentrum Leipzig-Halle GmbH, Leipzig, Germany

[21] Appl. No.: 09/011,091

[22] PCT Filed: Jul. 17, 1996

[86] PCT No.: PCT/EP96/03151

§ 371 Date: Mar. 27, 1998

§ 102(e) Date: Mar. 27, 1998

[87] PCT Pub. No.: WO97/05237

PCT Pub. Date: Feb. 13, 1997

[30] Foreign Application Priority Data

Jul. 28, 1995 [DE] Germany .......................... 195 29 021

[51] Int. Cl.⁷ ...................................................... C12S 13/00
[52] U.S. Cl. .................. 435/262.5; 435/248; 435/252.1; 210/611
[58] Field of Search ................................. 435/262, 262.5, 435/266, 248, 252; 210/601, 610, 611

[56] References Cited

U.S. PATENT DOCUMENTS 5,449,397  9/1995  Hunter et al. .
5,587,079  12/1996  Rowley et al. .

FOREIGN PATENT DOCUMENTS 4106781   9/1992  Germany .
62-193697 8/1987  Japan .
62193697  8/1987  Japan .
1-51195   2/1988  Japan .

OTHER PUBLICATIONS

Glombitza et al. Derwent Abstract No. 1992–141835 of DD 296263 (Nov. 1991).
Glombitza et al. Chemical Absract No. 116:200478 of DD 296264 (Nov. 1991).
W. Holl et al., Vom Wasser, 53:189 (1979).
U. Brettschneider, PhD Thesis (1990).
F. Bergman et al., Vom Wasser, 64:155 (1985).
D.J. Cork et al., Waste Treatment and Environmental Considerations, 207–221 (1978).
D.J. Cork et al., Rev. Ind. Microbiol., 20:591 (1979).
J.F. Spisak, Metallurgical Effluents–Growing Challenges for Second Generation Treatment, 23:249.
R.A. Uphaus et al., Dev. Ind. Microbiol., 24:435 (1983).
J.P. Maree et al., Environ. Technol. Lett., 8:53 (1987).
J.P. Maree et al., Water Sci. Technol., 21:265 (1989).
D. Tommerdich, PhD Thesis (1993).
Zellner et al., Arch Microbiol., 152:329 (1989).
Klemps et al., Arch. Microbiol., 143:203 (1985).
Isaksen et al., FEMS Microb. Ecol., 14:1 (19940).
Nanninga et al., FEMS Microbiol. Ecol., 38:125 (1986).
Nanninga et al., Appl. and Environ. Microbiol., 53:802 (1987).
Braun et al., Arch. Microbiol., 142:77 (1985).
J. Basic Microbiol., 35:385 (1995).
Arch. Microbiol., 147:163 (1987).

*Primary Examiner*—William H. Beisner
*Attorney, Agent, or Firm*—Birch, Stewart, Kolasch & Birch, LLP

[57] ABSTRACT

The present invention relates to Gram-negative sulfate-reducing bacteria strains which grow under anaerobic conditions at pH values between 3.9 and 9.5 and temperatures between 3° C. and 45° C. and which reduce sulfate to sulfide, utilize methanol as a source of carbon and energy, do not require further carbon and energy sources in addition to methanol, and are tolerant to metals. The present invention further relates to methods of decontaminating sulfuric-acid, metal-containing and radioactively contaminated water, particularly methods of decontaminating pit and flooding water in disused uranium mines or washing water from soil refining plants.

12 Claims, 3 Drawing Sheets

SULPHATE-REDUCING BACTERIAL STRAINS AND THEIR USE IN THE DECONTAMINATION OF WATER CONTAMINATED WITH SULPHURIC ACID, METALS AND RADIOACTIVE SUBSTANCES

This application is the national phase under 35 U.S.C. §371 of prior PCT International Application No., PCT/EP96/03151, which has an International filing date of Jul. 17, 1996, which designated the United States of America, the entire contents of which are hereby incorporated by reference.

The invention relates to the microbiological decontamination of sulfuric-acid, metal-containing, anaerobic, in some cases radioactively contaminated water using new Gram-negative sulfate-reducing bacteria.

The invention can be utilized in the treatment of pit and flooding water in disused mines, particularly uranium mines.

Sulfuric-acid and metal-containing water can be processed in various ways. Most of the procedures developed so far are based on physical and chemical principles. Thus, ion/anion exchange may be used in the purification of sulfate-containing water; however, this is unsuitable for flooding water because huge amounts of water have to be treated. In addition, neutralization and/or precipitation reactions are required. One drawback is that the plants are prone to misfunction due to biofouling [Höll, W. and Kiehling, B. (1979), Nitrat- and Sulfatentfernung aus Rohwässern durch Anionenaustausch, Vom Wasser 53, 189–202; Brettschneider, U. (1990), Die Bedeutung von Sulfaten in der Siedlungswasserwirtschaft und ihre Entfernung durch Desulfurikänten, PhD Thesis, Darmstadt].

When using the reverse osmosis procedure, pre-purification and conditioning are required. There is the problem of membrane blocking, and the volumes of water to be treated are excessively high for such type of treatment [Bergmann, F. (1984), Umkehrosmose zur Sulfatentfernung, Wasser, 105, 217–240; Bergman, F., Rüffer, H., Schneegans, R. and Slomka, T. (1985), Erste Erfahrungen mit der Umkehrosmose-Anlage Duderstadt zur Sulfatentfernung, Vom Wasser 64, 155–167].

The procedures described so far for sulfate reduction and metal precipitation by bacteria are multistep processes which are highly expensive with respect to the plant, and thus very costly, and are incapable of being performed at acidic pH, and use lactate, acetate or ethanol as the carbon source [Cork, D. C. and Cusanovich, M. A. (1978), Sulfate Decomposition, a Microbiological Process, Waste Treatment and Environmental Considerations, 207–221; Cork, D. C. and Cusanovich, M. A. (1979), Continuous Disposal of Sulfate by a Bacterial Mutualism, Rev. Ind. Microbiol. 20, 591–602; Spisak, J. F. (1979), Metallurgical Effluents—Growing Challenges for Second Generation Treatment, Dev. Ind. Microbiol. 20, 379–387; Uphaus, R. A., Grimm, D. and Cork, D. J. (1983), Gypsum Bioconversion to Sulphur: a Two-Step Microbiological Process, Dev. Ind. Microbiol. 24, 435–442; Maree, J. P., Gerber, A., McLaren, A. R. and Hill, E. (1987), Biological Treatment of Mining Effluents, Envi-ron.Technol. Lett. 8, 53–64; Maree, J. P. and Hill, E. (1989), Biological Removal of Sulphate from Industrial Effluents and Concomitant Production of Sulphur, Water Sci. Technol. 21, 265–276; Tommerdich, D. (1993), Entwicklung eines biotechnologischen Verfahrens zur Behandlung saurer sul-fatund metallhaltiger Wässer, PhD Thesis, Bonn].

Another method described in DE 4,106,781 A1 involves incorporating sewage sludges as nutrients for sulfate-reducing bacteria on garbage dumps. However, this process suffers from various drawbacks. Due to the incorporation of the nutrients into the garbage dump, the process operates without control and relies on seepage of the nutrients. The method is not suitable for metal removing and sulfate reduction in mine water.

It was the object of the invention to provide bacteria strains permitting decontamination of strongly sulfuric-acid (pH values between 1 and 2) and metal-contaminated water at low cost and effectively using a controlled one-step process in a fermenter. More specifically, the bacteria strains are designed to have the property of efficiently adsorbing and accumulating metals including radioactive elements such as uranium and radium, in order to be suitable, e.g., for mine water of disused uranium mines.

New mesophilic Gram-negative bacteria strains have been found which grow under anaerobic conditions at pH values between 3.9 and 9.5, preferably 4 and 9, and temperatures between 3 and 45° C., and reduce sulfate to sulfide. In particular, the bacteria strains of the invention are capable of utilizing methanol as a source of carbon and energy without requiring further sources of carbon and energy. In addition to methanol, these strains are also capable of utilizing electron donors such as pyruvate, lactate, acetate, ethanol, butanol, propanol, choline, betain, succinate, fumarate, and benzoate in their metabolism without the addition of hydrogen.

The strains of the invention tolerate metals and also adsorb and accumulate light metals such as aluminum in addition to heavy metals such as iron and radioactive metals such as uranium and radium.

Naturally occurring sulfate-reducing bacteria strains which reduce water-soluble sulfates to $H_2S$ and/or water-insoluble sulfides under certain conditions are known to operate their oxidative energy metabolism under anaerobic conditions and prefer low molecular weight organic materials ($C_\alpha H_\beta O_\gamma$) as electron donors in their metabolism.

There are some reports in the literature on sulfate-reducing bacteria capable of utilizing methanol as an electron donor. However, none of the strains described in the literature is identical to the strains according to the invention and/or requires only methanol as a source of carbon and energy without the need of further sources of carbon and energy or, e.g., vitamins.

Thus, Zellner et al., Arch. Microbiol. 152, (1989), pp. 329–334, describe that the marine species *Desulfovibrio salexigens* grows on methanol but requires sodium chloride to do so. *Desulfotomaculum orientis* is also a species utilizing methanol (Klemps et al., Arch. Microbiol. 143 (1985), pp. 203–208). However, they differ from the strains according to the invention in that they are Gram-positive strains incapable of utilizing acetate. In FEMS Microb. Ecol. 14 (1994), pp. 1–8, Isaksen et al. describe a strain P60 which, however, is thermophilic and shows optimum growth at 63° C. These strains are unsuitable for industrial use because of the higher temperatures to be provided. *Desulfovibrio carbinolicus* and a strain EDK 82, all isolated from a waste water treatment plant, are strains utilizing methanol as an electron donor but require acetate as a carbon source (Nanninga et al., FEMS Microbiol. Ecol. 38, (1986), pp. 125–130; Nanninga et al., Appl. Environ. Microbiol. 53 (1987), pp. 802–809). Similarly, the Desulfovibrio species require pyruvate as a source of carbon for growth (Braun et al., Arch. Microbiol. 142 (1985), pp. 77–80).

The strains according to the invention were isolated from the sludge of a waste water pool of the shut down sugar beet processing plant in Helmsdorf near Halle, Germany. Isolation was effected according to standard procedures known to the expert, and strain cultivation was conducted using anaerobic methods common in microbiology.

The bacteria strains according to the invention are remarkable for their broad pH range of from 3.9 to 9 and the temperature range of from 3 to 45° C., preferably from 5 to 40° C., wherein they grow and reduce sulfate to sulfide. Maximum growth rates range from 0.2 to 0.3 $h^{-1}$. The optimum temperature ranges from 25 to 30° C., and the optimum pH value is about 7.

The growth rates were determined by means of protein determination according to Bradford (Anal. Biochem. 72, pp. 248–254, 1976).

As a special feature it is to be noted that the strains according to the invention show good growth rates even at acidic pH values below 4.9 or alkaline pH values above 7.5.

As preferred bacteria strain, three strains designated UFZ B 378, UFZ B 406, and UFZ B 407 have been isolated and were deposited with the DSM (Deutsche Sammlung von Bakterien und Zellkulturen GmbH, Braunschweig, Germany) under the numbers 10,041 (UFZ B 378), 10,042 (UFZ B 406), and 10,043 (UFZ B 407) on Jun. 13, 1995 (06/13/1995).

As has been described, the bacteria strains according to the invention are anaerobic methylotrophic sulfate-reducing bacteria.

The cells of strain UFZ B 378 are linear to slightly bent rods and are mobile. Individual bacteria are between 1.5 and 3.5 μm in length and 0.5 μm in width. Growth takes place within a pH range of from 4.0 to 9.0, at temperatures between 3 and 40° C. The maximum growth rate is ca. 0.25 $h^{-1}$. The DNA G+C content is 58.7 mole % determined using HPLC according to the method of Mesbah et al., Int. J. System. Bacteriol. 39 (1989), pp. 159–167.

The cells of strain UFZ B 406 are vibrios from 2.9 to 3.9 μm in length and 1.1 to 1.5 μm in width. They grow within a pH range of from 6 to 8. The maximum growth rate is ca. 0.24 $h^{-1}$.

UFZ B 407 also has a vibriod cell form. Individual cells are from 3.1 to 4.0 μm in length and from 1.2 to 1.5 μm in width. Growth takes place between pH 6 and 9. The maximum growth rate is ca. 0.22 $h^{-1}$.

All of the three strains are Gram-negative and do not form spores. Methanol is used as a source of carbon and energy, and sulfate as an electron acceptor.

The described bacteria of the invention are excellently suited for the decontamination of anaerobic, sulfuric-acid, metal-containing, in some cases radioactively contaminated water. Thus, for instance, the pit and flooding water of disused uranium mines are highly radioactive due to naturally occurring uranium and radium, their pH values range from 1 to 2, and the water is high in sulfates and metals such as iron and aluminum. When mines are shut down, they are flooded, and the water reaching the surface must be decontaminated before it reaches the water ways.

Figure 2:
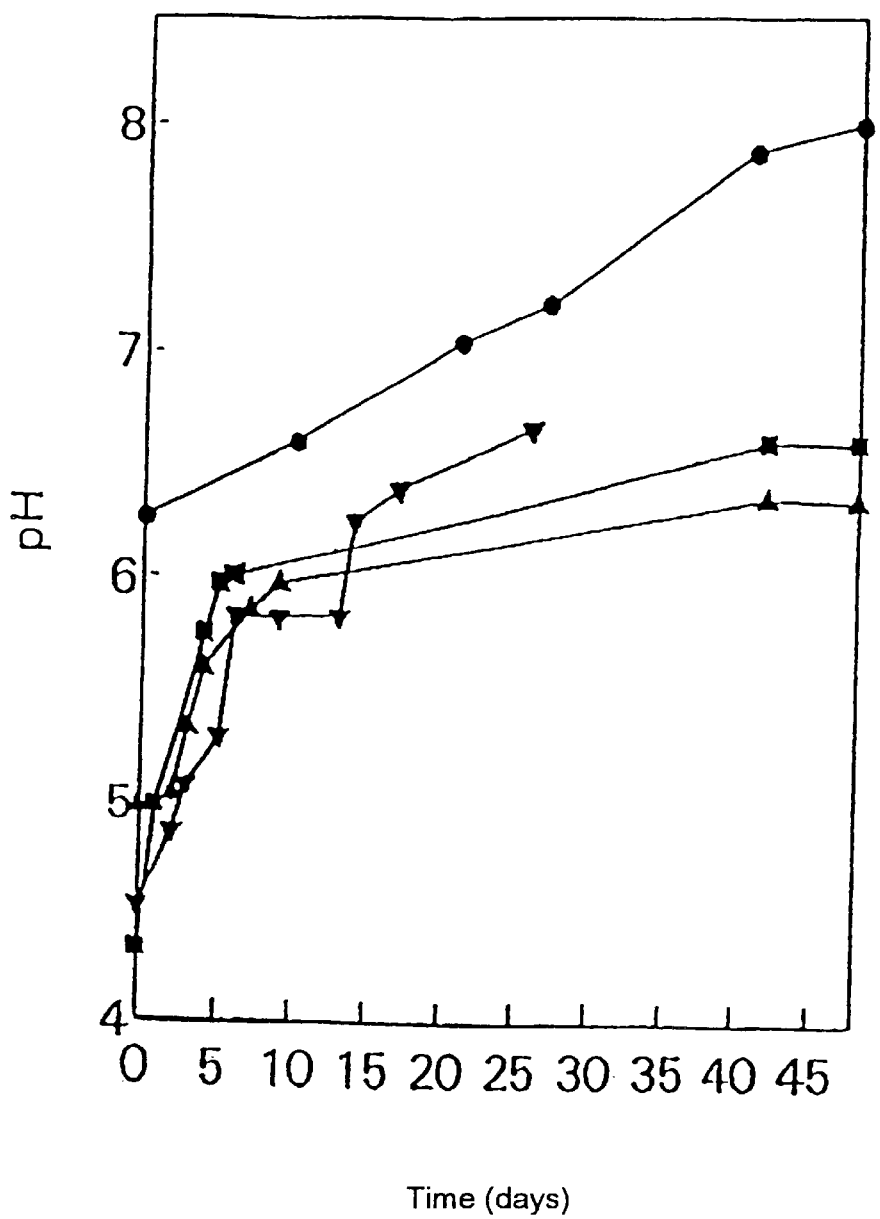

According to the invention, a process is therefore suggested, by which sulfate in said water is reduced to $H_2S$ by means of said found bacteria (in appropriate fermenters under anaerobic conditions), giving rise to an increase of the pH value. Sulfate reduction and increase of the pH value are illustrated in FIGS. 1 and 2, using the strain UFZ B 378 as an example. Due to the pH shift, the heavy metal ions are precipitated as sparingly soluble sulfides. In this process, sulfate plays the role of a terminal electron acceptor. The biomass formed serves as "adsorber and accumulator" for heavy metals, radioactive metals and also light metals (if present).

In order to make this process an economic one, it is important that the bacteria can utilize a source of carbon and energy which is low in cost and highly abundant. Methanol meets these requirements, and the special advantage of this process lies in the use of same. If methanol was only used for the purpose of reducing sulfate, 0.44 g of methanol would be required for 1 g of sulfate according to the following stoichiometry:

$$4CH_3OH + 3SO_4^{2-} + 2H^+ \rightarrow 4\ HCO_3^- + 3\ H_2S + 4\ H_2O.$$

Figure 3:
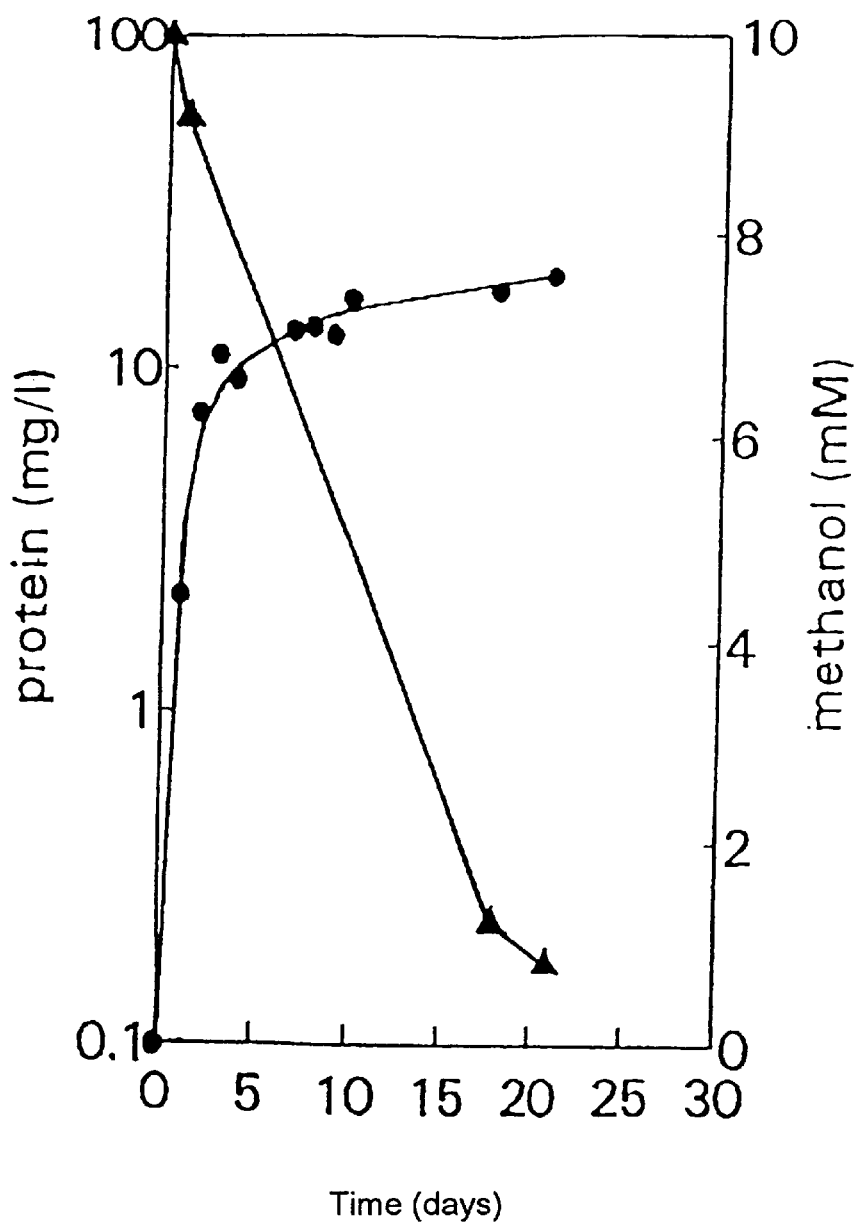

In reality, more methanol is consumed (cf., FIG. 3). Using this energy which is provided for biosyntheses as a result of the above redox reaction, methanol (the carbon thereof) is assimilated and emerges as bacterial biomass, the formation of which is desirable because it is required as a catalyst on the one hand and, on the other hand, acts as an "accumulator and/or adsorber" for heavy metals.

Since the energy gain is low, quite a lot of methanol must be oxidized in order to synthesize one unit of biomass, i.e., to achieve growth and expansion of the bacteria population. In theory, the amount of methanol consumed in the reduction of 1 g of sulfate is increased to at least 0.53 g, depending on the energy yield.

In comparison, if acetate would be used as the source of carbon and energy, which is possible in principle, at least 0.73 g would be required in order to reduce 1 g of sulfate, according to a theoretical estimation.

Similarly, about the same amount would be required if lactate—a source of carbon and energy for many sulfate-reducing bacteria—would be used.

These comparisons demonstrate the advantage of using methanol. Considering the costs for methanol on the one hand and of acetate and/or lactate on the other hand, the advantage of using methanol is even more significant.

Therefore, the invention also relates to a process for the microbiological decontamination of sulfuric-acid and metal-containing water by sulfate-reducing bacteria strains according to claims 7 through 9.

The decontamination of sulfuric-acid and metal-containing water may also be conducted as a batch, fed-batch or a continuous process. The decontamination process may be operated at temperatures between 3 and 40° C., preferably at 25 to 30° C. According to the invention, not only the new bacteria strains per se, but also mixtures thereof can be used in the disposal of sulfate- and metal-containing pit and flooding water.

Of course, sulfuric-acid, metal-containing water produced as washing water in soil refining plants may also be decontaminated by means of the process according to the invention, if the soils were treated with sulfuric acid for decontamination purposes.

Advantageously, the industrial process for refining contaminated water may be conducted in a reactor, e.g., a stirred container, thereby permitting monitoring and controlling the course of the process, i.e., optimizing the process parameters such as temperature but also the supply of the source of carbon and energy, so that optimum conditions are created for the advantageous bacteria strains for sulfate reduction.

FIGS. 1–3 illustrate:

FIG. 1: Sulfate reduction in the batch culture of the UFZ B 378 (determination in three cultures);

FIG. 2: Representative example of pH value increase in the methanol-consuming batch cultures of the UFZ B 378 strain as a function of time;

● Initial pH value 6.5; 10 mM methanol
∇ Initial pH value 4.5; 10 mM methanol
■ Initial pH value 4.3; 10 mM methanol
Δ Initial pH value 5.0; 31.25 mM methanol FIG. 3: Growth curve of the UFZ B 378 strain in the batch culture with 10 mM methanol as source of carbon and energy;

Determination in three cultures;

● Protein

Δ Methanol

In the following, the invention will be described in detail by way of examples not intended to be limiting.

EMBODIMENTS

EXAMPLE 1

The UFZ B 378 bacteria strain is cultivated in a fermenter under anaerobic conditions with nitrogen gas supply at 30° C. and a pH value of 7.0. The solution for nutrition is composed of 3 solutions:

Solution 1: 0.5 g of $FeSO_4.7H_2O$ in 10 ml of $H_2O$

Solution 2: 0.1 g of thioglycolic acid, 0.1 g of ascorbic acid, 20 mg of dithionite in 10 ml of distilled $H_2O$ Solution 3: 10 ml of 1M methanol, 2.0 g of $MgSO_4.7H_2O$, 1.0 g of $CaSO_4$, 1.0 g of $NH_4Cl$, 0.5 g of $KH_2PO_4$, 1.0 g of yeast extract in 1 l of distilled $H_2O$.

Cultivation of the strain is also possible without yeast extract.

During the growth of the above bacteria strain on methanol as a source of carbon and energy, sulfate is reduced to form sulfide. The specific sulfate reduction rate is about 2.7 g/g.h, with about 9.5 g of methanol being consumed and 1 g of biomass being formed. The thus resulting ratio of 0.66 methanol/1 $SO_4$ (g/g) is quite close to the calculated one of 0.54:1.

When using the bacteria strain for decontaminating sulfuric-acid and metal-containing water in accordance with the invention, reduction solution 2 is required only if the water are non-anaerobic, i.e., no reducing conditions are present. As a rule, the components of solution 3 such as phosphate and chloride are contained in water of disused mines or pits so that only methanol must be added as a source of carbon and energy under industrial conditions. Yeast may optionally be added for growth enhancement.

EXAMPLE 2

As in Example 1, the UFZ B 378 strain is grown on methanol as a source of carbon and energy, whereby in contrast to Example 1, the initial pH value is adjusted to 6.3. Under these conditions, no difference can be observed regarding the specific sulfate consumption rate and the methanol/sulfate ratio. However, the expected neutralization according to stoichiometry takes place, and the pH value shifts to 7.05 within 3 weeks. After another 7 days a pH value as high as 8.0 is reached.

EXAMPLE 3

The UFZ B 378 strain is grown as described in Example 1. In this case, the process is started at a pH value of 4.3. Under these conditions, the methanol/sulfate ratio becomes more unfavorable. Surprisingly, the growth efficiency is increased. The pH value increases rapidly; after one week a value of 6 is reached, and after 4 weeks 6.6.

EXAMPLE 4

As in Example 1, the UFZ B 406 strain is grown on methanol as a source of carbon and energy. The specific sulfate reduction rate is about 0.7 g/g.h. Accordingly, a sulfide formation rate of 0.23 g/g.h results. The iron content in the respective flooding water is ca. 500 mg per liter. In this example, the initial iron concentration is 1.44 g/l. With the above-mentioned sulfide formation rate, 0.82 g of iron was precipitated as sulfide after 2 hours, and even 9.84 g of iron/g of biomass after 24 hours.

EXAMPLE 5

The UFZ B 407 strain is grown as described in Example 1 but in contrast, 10 mM $Al_2(SO_4)_3$ is added. The concentration of dissolved aluminum is 1.05 mg/l. Sulfate is reduced at a rate of about 0.8 g/g.h, with aluminum being removed from the solution by adsorption and accumulation. An analysis reveals the biomass to be loaded with 0.69 mg/l, with 0.62 mg/l being located on the cell wall.

We claim:

1. Purified gram-negative sulfate-reducing bacteria strains, characterized in that they grow under anaerobic conditions at pH values between 3.9 and 9.5 and temperatures between 3 and 45° C. and reduce sulfate to sulfide, utilize methanol as a source of carbon and energy, do not require further sources of carbon and energy in addition to methanol, and are tolerant to metals.

2. The bacteria strains according to claim 1, characterized in that they have maximum growth rates between 0.2 and 0.3 $h^{-1}$.

3. The bacteria strains according to claim 1 or 2, characterized in that they are capable of adsorbing and accumulating radioactive metals and heavy metals as well as light metals.

4. The bacteria strain UFZ B 378 according to claim 1, deposited under deposition number DSM 10,041.

5. The bacteria strain UFZ B 406 according to claim 1, deposited under deposition number DSM 10,042.

6. The bacteria strain UFZ B 407 according to claim 1, deposited under deposition number DSM 10,043.

7. A process for the microbial decontamination of sulfuric-acid and metal-containing water by sulfate-reducing bacteria, characterized in that the new bacteria strains according to claim 1 are employed, the process is conducted under anaerobic conditions at pH values between 3.9 and 9.5 and temperatures between 3 and 45° C. and, in addition to common nutrient salts for sulfate-reducing bacteria, methanol is added as the only source of carbon and energy.

8. The process according to claim 7, characterized in that radioactively contaminated water is decontaminated.

9. The process according to one of claims 7 or 8, characterized in that washing water from soil refining plants is decontaminated.

10. The process according to claim 8, characterized in that said radioactively contaminated water is contaminated with uranium or radium.

11. The process according to claim 7, characterized in that highly sulfuric-acid, metal containing and radioactively contaminated water is decontaminated.

12. The process according to claim 11 characterized in that pit and flooding water of disused uranium mines is decontaminated.

* * * * *